United States Patent
Lok et al.

(10) Patent No.: US 6,927,190 B2
(45) Date of Patent: Aug. 9, 2005

(54) CATALYSTS WITH HIGH COBALT SURFACE AREA

(75) Inventors: Martinus C Lok, Guisborough (GB); Gordon J Kelly, Darlington (GB); Gavin Gray, Billingham (GB)

(73) Assignee: Johnson Matthey PLC, London (GB)

( * ) Notice: Subject to any disclaimer, the term of this patent is extended or adjusted under 35 U.S.C. 154(b) by 0 days.

(21) Appl. No.: 10/983,751

(22) Filed: Nov. 9, 2004

(65) Prior Publication Data

US 2005/0065025 A1 Mar. 24, 2005

Related U.S. Application Data

(63) Continuation of application No. 10/298,920, filed on Nov. 19, 2002, which is a continuation of application No. PCT/GB01/01811, filed on Apr. 23, 2001.

(30) Foreign Application Priority Data

May 19, 2000 (GB) .............................................. 0012087
Aug. 7, 2000 (GB) .............................................. 0019182

(51) Int. Cl.$^7$ ........................... B01J 23/00; B01J 20/00; B01J 21/00
(52) U.S. Cl. ........................ 502/327; 502/332; 502/355; 502/415; 502/439
(58) Field of Search .................................. 502/327, 332, 502/355, 415, 439

(56) References Cited

U.S. PATENT DOCUMENTS

| | | | | |
|---|---|---|---|---|
| 2,458,214 A | | 1/1949 | Souders, Jr. | |
| 4,024,075 A | * | 5/1977 | Russ et al. | 502/332 |
| 4,082,695 A | * | 4/1978 | Rosinski et al. | 502/220 |
| 4,255,357 A | | 3/1981 | Gardner et al. | |
| 4,314,913 A | * | 2/1982 | Derrien et al. | 502/354 |
| 4,419,275 A | * | 12/1983 | Yoshida et al. | 502/322 |
| 4,585,798 A | * | 4/1986 | Beuther et al. | 518/715 |
| 4,605,679 A | * | 8/1986 | Kobylinski et al. | 518/700 |
| 4,670,414 A | * | 6/1987 | Kobylinski et al. | 502/174 |
| 4,717,702 A | * | 1/1988 | Beuther et al. | 502/303 |
| 4,975,399 A | | 12/1990 | Gardner | |
| 5,036,032 A | | 7/1991 | Iglesia et al. | |
| 5,545,602 A | * | 8/1996 | Nelson et al. | 502/314 |
| 5,571,943 A | | 11/1996 | Borninkhof et al. | |
| 5,874,381 A | | 2/1999 | Bonne et al. | |
| 6,332,976 B1 | * | 12/2001 | Mignard et al. | 208/217 |
| 6,528,450 B2 | * | 3/2003 | Wu et al. | 502/240 |
| 6,534,436 B2 | | 3/2003 | Lok et al. | |
| 2003/0032684 A1 | | 2/2003 | Lok et al. | |
| 2003/0105170 A1 | | 6/2003 | Jothimurugesan et al. | |

FOREIGN PATENT DOCUMENTS

EP 0029675 3/1981
EP 0211545 2/1987

* cited by examiner

*Primary Examiner*—Cam N. Nguyen
(74) *Attorney, Agent, or Firm*—Mayer Brown Rowe & Maw LLP

(57) ABSTRACT

A catalyst or precursor thereto comprising cobalt and/or a cobalt compound on a transition alumina support having a total cobalt content of at least 41% by weight and a cobalt surface area, after reduction, greater than 25 m$^2$ per gram of total cobalt. The catalyst or precursor may be made by slurrying a transition alumina powder having a pore volume of at least 0.7 ml/g with an aqueous cobalt ammine carbonate complex and heating the slurry to decompose the complex.

6 Claims, No Drawings

CATALYSTS WITH HIGH COBALT SURFACE AREA

CROSS-REFERENCE TO RELATED APPLICATIONS

This application is a continuation of U.S. Ser. No. 10/298,920, filed Nov. 19, 2002, which is further a continuation of International Application No. PCT/GB01/01811, filed Apr. 23, 2001, which was published in English and designated the United States. These applications, in their entirety, are incorporated herein by reference.

This invention relates to catalysts and in particular to catalysts containing cobalt which are suitable for use in hydrogenation reactions.

Catalysts comprising cobalt on a support such as silica or alumina are known in the art for hydrogenation reactions, e.g. for the hydrogenation of aldehydes and nitriles and for the preparation of hydrocarbons from synthesis gas via the Fischer-Tropsch reaction.

In comparison with other catalytic metals such as copper and nickel used for hydrogenation reactions, cobalt is a relatively expensive and so, to obtain the optimum activity, it is desirable that as much as possible of the cobalt present is in an active form accessible to the reactants. For hydrogenation reactions, the active form of the cobalt is elemental cobalt although in the active catalyst only some, rather than all of the cobalt is normally reduced to the elemental form. Hence a useful measure is the exposed surface area of elemental cobalt per g of total cobalt present. Except where expressly indicated, as used herein, total cobalt contents are expressed as parts by weight of cobalt (calculated as cobalt metal, whether the cobalt is actually present as the metal or is in a combined form, e.g. as cobalt oxides) per 100 parts by weight of the catalyst or precursor thereto.

Cobalt catalysts on different carriers are disclosed in "Stoichiometries of $H_2$ and CO Adsorptions on cobalt", Journal of Catalysis 85, pages 63–77 (1984) at page 67, table 1. From the total maximum $H_2$ uptake, it is possible to calculate the cobalt surface area per gram of catalyst and the cobalt surface area per gram of cobalt. It can be seen from this reference that while the cobalt surface area per gram of total cobalt ranges between 6 and 65 $m^2/g$ for cobalt on silica catalysts, for cobalt on transition alumina catalysts, the cobalt surface area per gram of total cobalt ranges only between 15 and 26 $m^2/g$. However for some applications it is desirable to use alumina, rather than silica, as the support.

It has been proposed in EP 0 029 675 to make catalysts comprising 25 to 70% by weight, based upon the weight of the calcined and reduced catalyst, of a metal such as nickel and/or cobalt by coprecipitating the metal, together with aluminium, in the presence of porous particles such as gamma alumina particles. It is stated that cobalt-containing catalysts preferably contain 25 to 60% by weight of cobalt and that cobalt-containing catalysts may have cobalt surface areas, as determined by hydrogen chemisorption, in the range 5 to 20 $m^2$ per gram of catalyst. While a catalyst containing 25% by weight of cobalt and having a cobalt surface area of 20 $m^2$ per gram of catalyst, i.e. combining the extremities of the specified ranges, would have a cobalt surface area of 80 $m^2$ per gram of total cobalt, there is no suggestion that catalysts having such high cobalt surface areas per gram of total cobalt can in fact be made by the specified route. We have found that catalysts made by the procedure of Example 1 of EP 0 029 675 containing 26.4%, 37.0% and 52.1% total cobalt, based upon the weight of the unreduced catalyst, (corresponding to cobalt contents of 29%, 43% and 64% respectively in the reduced catalyst if it is assumed that all the cobalt in the reduced catalyst is present in the elemental form) have, upon reduction, cobalt surface areas of 8.2, 8.1 and 12.5 $m^2$ per g of unreduced catalyst, corresponding to cobalt surface areas of 31, 22 and 24 $m^2/g$ total cobalt respectively. This is indicative that the procedure of that reference does not provide a route to the production of catalyst having a high cobalt content that at the same time have a high cobalt surface area per g total cobalt.

U.S. Pat. No. 5,874,381 describes a cobalt on alumina catalyst which contains between 3 and 40% by weight of cobalt and which has a relatively high cobalt surface area of above 30 $m^2/g$ of total cobalt.

As indicated above, the dispersion of the cobalt on the carrier is important since it is the surface of the cobalt of the catalyst which is active. Therefore it is beneficial to maximise the surface area of the metal which is present so as to produce a catalyst which has a high cobalt surface area per unit mass of total cobalt. It may be expected that the dispersion of the cobalt on the catalyst would be maximised at relatively low loadings of cobalt and that, as the amount of cobalt contained in the catalyst is increased, the surface area per gram of cobalt would decrease because the cobalt becomes more difficult to disperse on the support.

For some applications, it is desirable to employ catalysts having a high loading of active material in order to minimise the amount of support. However under some conditions it is possible that the cobalt species may react with the alumina support to form a cobalt aluminate which is difficult to reduce. Indeed, formation of some cobalt aluminate may be desirable in order to provide a key for bonding the cobalt species to the alumina. However, because of the difficulty in reducing the cobalt aluminate, the cobalt aluminate formation decreases the amount of cobalt available for reduction to active elemental cobalt. By using a composition having a high loading of cobalt, a greater proportion of the cobalt species is available for reduction to the active elemental cobalt, even if a significant amount of the support alumina reacts with the cobalt species to form cobalt aluminate. Indeed, even if all the support alumina reacts with the cobalt species to form cobalt aluminate, a calcined catalyst precursor having a total cobalt content above about 41% by weight inevitably contains some cobalt in a form that is not so combined.

The aforementioned U.S. Pat. No. 5,874,381 suggests and exemplifies the production of the catalysts by impregnation of shaped transition alumina particles, e.g. extrudates, with a solution of cobalt ammine carbonate, followed by removal of the excess solution and heating to decompose the cobalt ammine carbonate. However we have found that it is difficult to obtain materials with a high cobalt content by this method. This reference also suggests, but does not exemplify, an alternative procedure wherein a slurry of transition alumina in a solution of the cobalt ammine carbonate is heated to cause the cobalt to precipitate as a hydroxycarbonate.

We have found that if the transition alumina has a relatively high pore volume, above 0.7 ml/g, preferably above 0.75 ml/g, then it is possible to achieve high cobalt loadings, and the resultant catalysts, upon reduction, have a relatively high cobalt surface are per gram of total cobalt. Preferably the transition alumina has a pore volume in the range 0.7 to 1.2 ml/g.

Thus we have now found that compositions containing more than 40% cobalt by weight may be made which, upon reduction, have a cobalt surface area of greater than 25 $m^2/g$ of total cobalt.

Accordingly the invention provides a catalyst, or precursor thereto, comprising a cobalt species on a transition alumina support characterised in that the catalyst, or precursor, has a total cobalt content of at least 41% by weight and that, after reduction, has a cobalt surface area greater than 25 m$^2$/g of total cobalt.

The term "cobalt species" is used broadly to include both elemental cobalt and cobalt in combined form, e.g. as compounds such as cobalt oxides and cobalt hydroxycarbonates. The catalyst in its reduced form is useful for catalysing hydrogenation reactions. The catalyst may, however, be provided as a precursor wherein the cobalt is present as one or more compounds, such as oxides or hydroxy carbonates, reducible to elemental cobalt. In this form, the material may be a catalyst precursor and may be treated to reduce the cobalt compounds to metallic cobalt or the material may itself be a catalyst and used as supplied, e.g. for oxidation reactions. The cobalt surface area figures used herein apply to the material after reduction, but the invention is not limited to the provision of reduced catalyst.

As indicated above, the compositions of the invention may be made by the procedure of the aforesaid U.S. Pat. No. 5,874,381 by utilising a transition alumina having a relatively large pore volume. It will be appreciated that the use of a large pore volume alumina may also be beneficial when making products having a smaller cobalt content.

Accordingly we also provide a method of making a cobalt/alumina catalyst or precursor thereto containing 5 to 85% by weight of total cobalt comprising slurrying a transition alumina powder having a pore volume above 0.7 ml/g with an aqueous solution of a cobalt ammine complex, heating the slurry to cause the cobalt ammine complex to decompose with the deposition of an insoluble cobalt compound, filtering the solid residue from the aqueous medium, drying and, optionally calcining, the solid residue.

The transition alumina may be of the gamma-alumina group, for example a eta-alumina or chi-alumina. These materials may be formed by calcination of aluminium hydroxides at 400 to 750° C. and generally have a BET surface area in the range 150 to 400 m$^2$/g. Alternatively, the transition alumina may be of the delta-alumina group which includes the high temperature forms such as delta- and theta-aluminas which may be formed by heating a gamma group alumina to a temperature above about 800° C. The delta-group aluminas generally have a BET surface area in the range 50 to 150 m$^2$/g. The transition aluminas contain less than 0.5 mole of water per mole of $Al_2O_3$, the actual amount of water depending on the temperature to which they have been heated.

In order to obtain a catalyst that is of practical use, it is generally desirable that there is some interaction between the cobalt and the alumina support. Such interaction, which can be considered to be the formation of a cobalt aluminate, is desirable to "anchor" the cobalt and to prevent leaching of cobalt in use and/or coalescence of cobalt particles. Such leaching and/or coalescence would result in loss of catalytic activity. However, as indicated above, the cobalt aluminate interaction product is difficult to reduce, and so in catalysts having low cobalt contents a significant proportion of the cobalt may be in an unreducible form. It is therefore preferred to use such an amount of cobalt that the catalyst or precursor contains at least 20% by weight of cobalt.

Catalysts made by the conventional impregnation route typically impregnate the support material with an aqueous solution of a cobalt salt, typically cobalt nitrate. Such solutions have a low pH and to obtain some interaction between the cobalt and support, it is desirable to use a reactive alumina, especially gamma-alumina. However, where the cobalt is deposited via a cobalt ammine solution, the solutions have a high pH and under such conditions it is possible to obtain adequate interaction using less reactive aluminas, for example delta-alumina. If the proportion of cobalt ammine solution is relatively small so that products having relatively low cobalt contents are obtained, then, if gamma-alumina is employed, a relatively large proportion of the cobalt, for example 40% or more thereof, may interact with the alumina and so the reduced catalyst obtained from such materials will have a relatively low cobalt surface area.

However the less reactive aluminas such as delta-aluminas generally have a lower pore volume than the reactive gamma aluminas. Consequently it may be difficult to make catalysts based upon theta-alumina containing large amounts of cobalt. At high cobalt contents, above 50% by weight, it may therefore be desirable to employ a large pore volume gamma-alumina despite the greater reactivity of the alumina. As the cobalt loading increases, the disadvantages resulting from increased interaction between the cobalt and the reactive alumina become less significant compared to the advantages of the ability of obtaining high cobalt loadings by using high pore volume gamma-aluminas.

The transition alumina powder generally has a surface-weighted mean diameter D[3,2] in the range 1 to 200 μm. In certain applications such as for catalysts intended or use in slurry reactions, it is advantageous to use very fine particles which are, on average, preferably less than 20 μm, e.g. 10 μm or less. For other applications e.g. as a catalyst for reactions carried out in a fluidised bed, it may be desirable to use larger particle sizes, preferably in the range 50 to 150 μm. The term surface-weighted mean diameter D[3,2], otherwise termed the Sauter mean diameter, is defined by M. Alderliesten in the paper "A Nomenclature for Mean Particle Diameters"; Anal. Proc., vol. 21, May 1984, pages 167–172, and is calculated from the particle size analysis which may conveniently be effected by laser diffraction for example using a Malvern Mastersizer.

It is preferred that the alumina powder has a relatively large average pore diameter as the use of such aluminas appears to give catalysts of particularly good selectivity. Preferred aluminas have an average pore diameter of at least 10 nm, particularly in the range 15 to 30 nm. [By the term average pore diameter we mean 4 times the pore volume as measured from the desorption branch of the nitrogen physisorption isotherm at 0.98 relative pressure divided by the BET surface area]. During the production of the compositions of the invention, cobalt compounds are deposited in the pores of the alumina, and so the average pore diameter of the composition will be less than that of the alumina employed, and decreases as the proportion of cobalt increases. It is preferred that the catalysts or precursors have an average pore diameter of at least 8 nm, preferably above 15 nm and particularly in the range 15 to 25 nm.

It has been found that the bulk of the cobalt is precipitated as cobalt compounds within the pores of the transition alumina and only a small proportion of the cobalt is deposited as a coating round the alumina particles. As a result, irrespective of the cobalt content of the composition, the particle size of the compositions of the invention is essentially the same as the particle size of the transition alumina, and so the compositions of the invention generally have a surface-weighted mean diameter D[3,2] in the range 1 to 200 μm, in one embodiment preferably less than 100 μm and particularly less than 20 μm, e.g. 10 μm or less, and in a second embodiment preferably in the range 50 to 150 μm.

On the other hand, since the cobalt compounds are primarily precipitated within the pores of the transition alumina, the pore volume of the compositions in accordance with the invention will be less than that of the transition alumina employed, and will tend to decrease as the cobalt species loading increases. Compositions having a total cobalt content less than 30% by weight preferably have a pore volume of at least 0.5 ml/g while compositions having a total cobalt content above 30% by weight, particularly above 40% by weight, preferably have a pore volume of at least 0.3 ml/g, particularly at least 0.4 ml/g.

Accordingly the present invention also provides a particulate cobalt/transition alumina catalyst, or precursor thereto, having a total cobalt content of 5 to 85% by weight, a pore volume above 0.5 ml/g, a cobalt surface area, after reduction, of at least 25 m$^2$ per gram of total cobalt, and a surface-weighted mean diameter D[3,2] in the range 1 $\mu$m to 200 $\mu$m.

At high cobalt loadings, above 40% by weight, even if a large pore volume transition alumina is employed, the amount of cobalt species deposited within the pores may be such that the pore volume of the compositions is less than 0.3 ml/g. However, useful catalysts and precursors can be produced if the surface-weighted mean diameter D[3,2] of the alumina, and hence the precursor and/or catalyst, is relatively small, below about 20 $\mu$m.

Accordingly the present invention also provides a particulate cobalt/transition alumina catalyst, or precursor thereto, having a total cobalt content greater than 40% by weight, a surface-weighted mean diameter D[3,2] below 20 $\mu$m and having, in the reduced state, a cobalt surface area greater than 25 m$^2$/g of cobalt.

The compositions preferably contain 41 to 85%, more preferably 45 to 75%, by weight of cobalt.

The compositions of the invention, when in the reduced state, have a cobalt surface area of at least 25 m$^2$/g of cobalt as measured by the H$_2$ chemisorption technique described herein. Preferably the cobalt surface area is greater than 30, more preferably at least 40, especially at east 60 m$^2$/g. The cobalt surface area tends to decrease as higher loadings of cobalt are used, but we have found that when the composition contains 50 to 60% by weight total cobalt, the cobalt surface area achievable is about 80 m$^2$/g or more.

The cobalt surface area is determined by H$_2$ chemisorption. The sample (about 0.5 g) is degassed and dried under vacuum at 120° C. and then reduced by heating to 425° C. at a rate of 3° C. per minute whilst hydrogen gas is passed through the sample at a flow rate of 250 ml/min for 18 hours. The sample is then heated under vacuum to 450° C. over 10 minutes and maintained under those conditions for 2 hours. Following this pre-treatment, the chemisorption analysis is carried out at 150° C. using pure H$_2$ gas. The full isotherm is measured up to 800 mm Hg pressure of H$_2$ and the straight line portion of the chemisorption isotherm between 300 and 800 mm Hg is extrapolated to zero pressure to calculate the volume of the gas (V) which is chemisorbed by the sample. The metal surface area is then calculated from the following equation:

$$\text{Co surface area} = (6.023 \times 10^{23} \times V \times SF \times A)/22414$$

where V=uptake of H$_2$ in ml/g
SF=Stoichiometry factor (assumed 2 for H$_2$ chemisorption on Co)
A=area occupied by one atom of cobalt (assumed 0.0662 nm$^2$)

This method of calculating cobalt surface area is described in the Operators Manual for the Micromeritics ASAP 2000 Chemi System V 1.00, Appendix C, (Part no 200-42808-01, 18$^{th}$ Jan. 1991)

The compositions may be made by slurrying the transition alumina powder with the appropriate amount of an aqueous solution of a cobalt ammine complex, e.g. the product of dissolving basic cobalt carbonate in a solution of ammonium carbonate in aqueous ammonium hydroxide, to give a product of the desired cobalt content. The solution of the cobalt ammine complex preferably has a pH in the range 7 to 12. The slurry is then heated, e.g. to a temperature in the range 60 to 110° C., to cause the cobalt ammine complex to decompose with the evolution of ammonia and carbon dioxide and to deposit an insoluble cobalt compound, e.g. basic cobalt carbonate (cobalt hydroxycarbonate) on the surface, and in the pores, of the transition alumina. The alumina carrying the deposited cobalt compound is then filtered from the aqueous medium and dried. The procedure may be repeated, i.e. the dried product may be re-slurried in a solution of the cobalt ammine complex, heated, filtered and dried, if required to increase the cobalt content of the product.

The time allowed for the precipitation of the cobalt compound is normally about 30 to 200 minutes; the precipitation is usually complete after about 60 to 80 minutes, but the heating of the slurry may be prolonged to include an ageing step. During such an ageing step, it is believed that some of the cobalt is converted to cobalt aluminate compounds by reaction with the alumina support. The cobalt aluminate compounds are beneficial in that they may promote adhesion between the deposited cobalt compounds and the alumina support and thereby stabilise the catalyst. However these cobalt aluminate compounds are not catalytically active and may reduce the available cobalt surface area somewhat. Therefore it is necessary to select an appropriate process time to enable the formation of some limited amount of cobalt aluminate to take place without significantly reducing the available surface area. We have found that when the cobalt content is relatively low, e.g. up to about 40% by weight, it is beneficial to use relatively short process times, e.g. by limiting the total heating time, i.e. for both the precipitation and any ageing to 200 minutes or less, preferably less than 150 minutes. As the cobalt content of the catalyst is increased, the catalysts lose less of their surface area to cobalt aluminate formation and longer process times may be used, e.g. up to about 350 minutes.

Accordingly the present invention also provides a method of making a cobalt/alumina catalyst or precursor thereto containing 5 to 40% by weight of total cobalt comprising slurrying a transition alumina powder with an aqueous solution of a cobalt ammine complex, heating the slurry for a period of not more than 200 minutes to cause the cobalt ammine complex to decompose with the deposition of an insoluble cobalt compound, filtering the solid residue from the aqueous medium, drying and, optionally calcining, the solid residue.

For some applications it may be desired to incorporate modifiers, such as other metals or compounds thereof, into the catalyst or precursor. This may be effected by impregnating the dried product with a solution of a compound of the desired modifier that decomposes to the oxide or elemental form upon heating. Examples of such modifiers include alkali metals, precious metals, and transition metals such as rhenium.

If desired, the product may be calcined in air, e.g. at a temperature in the range 200 to 600° C., more preferably 200 to 450° C., to decompose the deposited cobalt compound to cobalt oxide. Upon reduction of the cobalt oxide, the high cobalt surface area is generated. Alternatively the deposited cobalt compound may be directly reduced, i.e. without the need for a calcination step. The reduction, whether or not a preliminary calcination step is employed, may be effected by heating to a temperature in the range from about 200° C. to about 600° C. in the presence of hydrogen. In the reduced material it is preferred that at least 50% of the cobalt is present as metallic cobalt.

The composition may be supplied in its oxidic state, i.e. without reducing the cobalt oxides to metallic cobalt. It may be used as a catalyst in this state for e.g. oxidation reactions or it may be a precursor and reduced to an active catalyst by the end-user. The composition may alternatively be supplied as a reduced catalyst which has been passivated, so that the cobalt metal is protected from deactivation during storage and transportation.

Alternatively, in some cases the reduction may be effected in situ. Thus a precursor comprising the transition alumina and the unreduced cobalt compound, e.g. oxide, possibly dispersed in a carrier, may be charged to a hydrogenation reactor with the material to be hydrogenated and the mixture heated while hydrogen is sparged through the mixture.

The catalysts may be used for hydrogenation reactions such as the hydrogenation of olefinic compounds, e.g. waxes, nitro or nitrile compounds, e.g. the conversion of nitrobenzene to aniline or the conversion of nitriles to amines. They may also be used for the hydrogenation of paraffin waxes to remove traces of unsaturation therein. They may also be useful in a wide range of other reactions, for example the Fischer-Tropsch process, i.e. where hydrogen and carbon monoxide are reacted in the presence of the catalyst to form higher hydrocarbons. This may be part of an overall process for the conversion of natural gas to petroleum compounds wherein the hydrogen/carbon monoxide gas mixture is a synthesis gas formed by steam reforming natural gas.

The invention will be further described in the following experimental examples.

EXAMPLE 1

A 4 litre aqueous stock solution was made up with 1916 g ammonia solution (SG 0.89, 30% ammonia), 198 g ammonium carbonate, 218 g basic cobalt carbonate and 1877 g demineralised water.

The alumina employed was a transition-alumina of the gamma alumina type having a surface area of about 145 ml /g and a pore volume of about 0.85 $m^2$/g and having a surface-weighted mean diameter D[3,2] of 2.08 μm, supplied by Sumitomo. The average pore diameter was about 23 nm.

The alumina particles and a measured amount of the stock solution were charged to a stirred vessel equipped with a condenser. The pH of the aqueous solution was 11.1. The mixture was heated to boiling while stirring and gentle boiling at about 96° C. was maintained for a period of time, during which the solution became clear after about 90 min. The total heating time is shown in the following table. The solid was then filtered off, washed and then dried in air at 120° C. overnight.

The resultant catalyst precursor was then reduced by passing hydrogen through a bed of the catalyst while heating to 430° C. The surface-weighted mean diameter of the reduced catalyst particles was similar to that of the transition alumina employed.

The cobalt content of the reduced catalyst was calculated from the measured cobalt content of the unreduced material and the weight difference between the unreduced material and the reduced catalyst. The relative amount of alumina and stock solution was varied to provide compositions having different cobalt contents. The results are shown in Table 1.

TABLE 1

| alumina/cobalt weight ratio | End pH | Total heating time (min) | Cobalt content (wt %) | | Cobalt surface area | |
|---|---|---|---|---|---|---|
| | | | unreduced product | reduced product | $m^2$ per gram reduced product | $m^2$ per gram cobalt |
| 1.75 | 8.56 | 180 | 27.2 | 32.1 | 27.1 | 84.4 |
| | 8.50 | 210 | 28.7 | 33.7 | 25.9 | 76.8 |
| | 8.78 | 240 | 28.7 | 33.3 | 22.1 | 66.3 |
| | 8.55 | 270 | 27.9 | 32.1 | 19.7 | 61.4 |
| | 8.32 | 300 | 28.6 | 32.8 | 17.7 | 53.9 |
| | 8.20 | 330 | 29.6 | 33.6 | 13.5 | 40.2 |
| 1.40 | 8.5 | 180 | 30.3 | 36.4 | 34.9 | 95.9 |
| | 8.38 | 240 | 32.2 | 39.1 | 34.4 | 87.9 |
| | 7.2 | 360 | 32.5 | 37.4 | 15.9 | 42.5 |
| 1.00 | 8.27 | 240 | 37.0 | 47.3 | 39.1 | 82.6 |
| | 8.12 | 300 | 36.7 | 47.1 | 36.9 | 78.4 |
| | 7.01 | 360 | 36.9 | 44.9 | 22.8 | 50.7 |
| 0.50 | 8.90 | 180 | 41.6 | 55.2 | 41.9 | 75.9 |
| | 8.31 | 240 | 41.0 | 54.8 | 41.7 | 76.1 |
| | 7.99 | 300 | 46.8 | 62.3 | 38.6 | 61.9 |
| 0.35 | 8.34 | 180 | 52.4 | 70.6 | 29.0 | 41.1 |
| | 8.24 | 240 | 53.3 | 72.8 | 30.7 | 42.2 |
| | 8.36 | 300 | 54.6 | 75.4 | 33.6 | 44.6 |
| 0.25 | 8.4 | 180 | 56.8 | 78.5 | 30.5 | 38.9 |
| | 7.9 | 240 | 56.5 | 78.5 | 23.4 | 29.8 |
| | 7.45 | 300 | 55.7 | 77.3 | 35.7 | 46.2 |
| 0.15 | 8.13 | 180 | 60.6 | 86.9 | 21.0 | 24.2 |
| | 7.99 | 240 | 61.1 | 87.0 | 19.8 | 22.7 |
| | 7.26 | 300 | 61.5 | 85.9 | 22.4 | 26.1 |

It is clear from the examples that when the amount of cobalt is relatively low, ageing may be harmful and shorter processing times may be preferred in those cases.

The BET surface areas and pore volumes of the unreduced materials made using the alumina to cobalt weight ratio 1.75 was determined and are shown in the following Table 2.

TABLE 2

| Total heating time (min) | Cobalt content (wt %) | BET surface area (m²/g) | Pore volume (ml/g) |
|---|---|---|---|
| 180 | 27.2 | 142 | 0.69 |
| 210 | 28.7 | 142 | 0.68 |
| 240 | 28.7 | 160 | 0.56 |
| 270 | 27.9 | 170 | 0.56 |
| 300 | 28.6 | 172 | 0.55 |
| 330 | 29.6 | 179 | 0.51 |

EXAMPLE 2

The activity for the Fischer-Tropsch reaction was assessed using catalysts of the invention and compared with prior art catalysts. The materials tested were as follows.

Catalyst A.

A sample of the unreduced material of Example 1 produced with an alumina to cobalt weight ratio of 1.75 and a total heating time of 270 min (unreduced cobalt content 27.9% by weight) was formed into pellets which were then broken up and screened.

Catalyst B

A sample of the unreduced material of Example 1 produced with an alumina to cobalt weight ratio of 0.5 and a total heating time of 240 min (unreduced cobalt content 41% by weight) was formed into pellets which were then broken up and screened.

Catalyst C1 (Comparative)

A precursor was made in accordance with the examples of U.S. Pat. No. 5,874,381 by multi-stage impregnation of trilobal extrudates of 1.2 mm length and 1.3 mm average diameter made from gamma-alumina with a cobalt ammine carbonate complex solution followed by heating to decompose the cobalt ammine carbonate. The precursor had a cobalt content of 15.1% and upon reduction gave a catalyst having a cobalt surface area of 79 m²/g total cobalt.

Catalyst C2 (Comparative)

A precursor containing 16.7% by weight cobalt was made by one-step impregnation of trilobal extrudates as used to make Catalyst C1 with an aqueous cobalt nitrate solution followed by drying at 120° C. for 15 hours and calcination at 300° C. for 10 hours. Upon reduction the catalyst had a cobalt surface area of 28.1 m²/g total cobalt.

Catalyst C3 (Comparative)

A precursor containing 17.8% by weigt cobalt, 0.43% ruthenium, and 1% lanthanum was made by was made by impregnating trilobal extrudates as used to make Catalyst C1 with an aqueous solution of cobalt nitrate, drying at 120° C. for 15 h, impregnating the dried impregnated extrudates with a solution of ruthenium acetylacetonate and lanthanum nitrate in a mixture of 2 parts by volume acetone to 1 part by volume ethanol, removing the organic solvent using a rotary evaporator under vacuum at 25° C. and then calcining the product at 300° C. for 10 h. Upon reduction the catalyst had a cobalt surface area of 43.9 m²/g total cobalt.

For Catalysts C1, C2 and C3, before testing, the impregnated trilobal extrudates were broken up and the particles screened.

For all the following activity tests, particles having a size in the range 0.25 to 0.42 μm were selected for testing.

The catalysts were tested using an isothermal reactor of internal diameter 7.5 mm with a catalyst bed length of 8 cm. The temperature of the catalyst bed was controlled by external heating responsive to a thermocouple disposed in the middle of the catalyst bed 4 cm from the bed inlet.

1 g of the precursor particles were mixed with silicon carbide particles having a similar size as diluent. The volume of silicon carbide particles used was 2.5 times the volume of the precursor particles. The mixture was charged to the reactor to form the catalyst bed and then the precursor was reduced by passing a stream of hydrogen at atmospheric pressure through the reactor at a rate of 24 litres (at NTP) per hour while increasing the temperature from ambient to 120° C., maintaining it at that temperature of 1 hour, then increasing the temperature to 300° C. at a rate of 100° C./h and maintaining it at that temperature for 4 hours. For Catalysts A and B, after the 1 hour at 120° C., the temperature was increased at a rate of 180° C./h to 460° C. (instead of 300° C.), and maintained at that temperature for 2 hours. [The higher reduction temperature was used for Catalysts A and B since it is believed that these catalysts have smaller cobalt-containing crystallites and these are more difficult to reduce than larger crystallites. It is believed that reducing the comparative catalysts C1, C2 and C3 at higher temperatures would not show any advantage therefor]

After reduction, the temperature was decreased to 220° C. and the pressure increased to 20 bar abs. Carbon monoxide and argon (as an internal analysis standard) were then incrementally added to the hydrogen and the flow rate adjusted until the feed gas volume composition was 60% hydrogen, 30% carbon monoxide and 10% argon and the total flow rate was 14.6 litres/h.

The conditions were maintained and the gas mixture leaving the reactor was continuously analysed.

When steady state conditions had been achieved, Catalysts C1, C2 and C3 gave carbon monoxide conversions of about 10, 18, and 28% respectively with the product distribution shown in the following Table 3. However the catalysts of the invention, Catalysts A and B, gave complete conversion of the carbon monoxide to methane, showing that while the catalysts were a good methanation catalysts, they were too active for use under those conditions as Fischer-Tropsch catalysts. Further investigation revealed that, with Catalyst A, although the temperature of the centre of the catalyst bed was controlled at 220° C., the initial portion of the bed had been heated by the exothermic reaction to a significantly higher temperature, namely about 300° C.

In the following Table, also quoted is the chain growth probability, $\alpha$, which is obtained from the equation $W_n/n = (1-\alpha)^2 \alpha^{n-1}$ where $W_n$ is the weight fraction of products containing n carbon atoms.

TABLE 3

| | Catalyst | | |
|---|---|---|---|
| | C1 | C2 | C3 |
| Precursor cobalt content (% wt) | 15.1 | 16.7 | 17.8 |
| Cobalt surface area (m²/g cobalt) | 79 | 28 | 44 |
| Average CO conversion (%) | 10 | 18 | 28 |
| Carbon products distribution | | | |
| carbon dioxide (wt %) | 5 | 3 | 4 |
| alcohols (wt %) | 11 | 4 | 5 |

TABLE 3-continued

| | Catalyst | | |
|---|---|---|---|
| | C1 | C2 | C3 |
| methane (wt %) | 16 | 13 | 20 |
| $C_2$ to $C_4$ hydrocarbons (wt %) | 6 | 10 | 15 |
| $C_5$ to $C_{12}$ hydrocarbons (wt %) | 44 | 45 | 47 |
| $C_{13}$ to $C_{18}$ hydrocarbons (wt %) | 15 | 14 | 6 |
| $C_{19+}$ hydrocarbons (wt %) | 3 | 11 | 3 |
| chain growth probability, α | 0.77 | 0.82 | 0.76 |

It is seen that despite its high cobalt surface area, Catalyst C1, made in accordance with U.S. Pat. No. 5,874,381, has a poor activity, giving a much lower carbon monoxide conversion than either Catalysts C2 and C3.

However, when tested by the same procedure but at a lower gas flow rate (about 5 litres/h), Catalyst C1 cave a carbon monoxide conversion of about 25% and a product distribution similar to that specified in Table 3 for Catalyst C2, but giving 2 slightly higher proportion of the higher hydrocarbons ($C_{13+}$) at the expense of the $C_5$ to $C_{12}$ hydrocarbons.

In order to overcome the apparent overheating of Catalyst A, the test procedure was repeated using Catalysts A, B and C3 but moving the thermocouple used to control the bed temperature to a position 1.5 cm from the bed inlet. Also, after reduction, the temperature was decreased to 190° C., instead of 220° C. and the pressure increased to 20bar abs. Carbon monoxide and argon (as an internal analysis standard) were then incrementally added to the hydrogen and the flow rate adjusted until the feed gas volume composition was 60% hydrogen, 30% carbon monoxide and 10% argon. Then the temperature was increased at a rate of 2° C./min to the test temperature of 220° C. The total flow rate employed, the productivity defined as the weight of hydrocarbons containing 11 or more carbon atoms produced per gram of catalyst precursor per hour, and the product distribution, are set out in the following Table 4.

TABLE 4

| | Catalyst | | | | | | |
|---|---|---|---|---|---|---|---|
| | A | | | | B | | C3 |
| Precursor cobalt content (% wt) | 27.9 | | | | 41 | | 17.8 |
| Cobalt surface area ($m^2$/g cobalt) | 61 | | | | 81 | | 44 |
| Space velocity (Nl/g precursor/h) | 16 | 46 | 67 | 90 | 29 | 61 | 15 |
| Average CO conversion (%) | 59 | 23 | 16 | 14 | 78 | 20 | 22 |
| $C_{11+}$ productivity (g/g precursor/h) | 1.2 | 1.2 | 0.7 | 0.9 | 2.9 | 1.6 | — |
| Carbon products distribution | | | | | | | |
| carbon dioxide (wt %) | 7 | 2 | 2 | 2 | 20 | 2 | 2 |
| Alcohols (wt %) | 2 | 3 | 3 | 3 | 2 | 7 | 6 |
| Methane (wt %) | 20 | 22 | 12 | 10 | 30 | 23 | 20 |
| $C_2$ to $C_4$ hydrocarbons (wt %) | 12 | 12 | 7 | 6 | 12 | 11 | 16 |
| $C_5$ to $C_{12}$ hydrocarbons (wt %) | 33 | 42 | 31 | 29 | 26 | 33 | 40 |
| $C_{13}$ to $C_{18}$ hydrocarbons (wt %) | 13 | 11 | 16 | 15 | 6 | 11 | 9 |
| $C_{19+}$ hydrocarbons (wt %) | 13 | 8 | 29 | 35 | 4 | 13 | 7 |
| α - chain growth probability | 0.84 | 0.81 | 0.89 | 0.92 | 0.78 | 0.83 | 0.79 |

It is seen that Catalysts A and B in accordance with the invention are much more active than Catalyst C3 and gave useful product distributions. Also Catalyst B is more active than Catalyst A.

What is claimed is:

1. A particulate catalyst precursor comprising cobalt compounds supported on a transition alumina support and having a total cobalt content of 20 to 85% by weight, a pore volume above 0.5 ml/g, and a surface-weighted mean diameter D[3,2] in the range 1 μm and which, upon reduction, has a cobalt surface area of at least 40 $m^2$ per gram of total cobalt.

2. A catalyst precursor according to claim 1 having a total cobalt content above 40% by weight.

3. A catalyst precursor according to claim 1 having a surface-weighted mean diameter D[3,2] below 20 μm.

4. A catalyst precursor according to claim 1 having an average pore diameter of at least 8 nm.

5. A catalyst precursor according to claim 1 wherein the cobalt is present as cobalt oxides.

6. A catalyst presursor according to claim 1 having a total cobalt content above 50% by weight and wherein the alumina is a gamma alumina.

* * * * *

UNITED STATES PATENT AND TRADEMARK OFFICE
CERTIFICATE OF CORRECTION

PATENT NO. : 6,927,190 B2
DATED : August 9, 2005
INVENTOR(S) : Cornelis M. Lok et al.

It is certified that error appears in the above-identified patent and that said Letters Patent is hereby corrected as shown below:

Title page,
Item [75], Inventors, "Martinus C. Lok" should be -- C. Martinus Lok --.

Column 12,
Line 35, "in the range 1 $\mu$m" should be -- in the range 1 $\mu$m to 200 $\mu$m --.

Signed and Sealed this

Twenty-eighth Day of February, 2006

JON W. DUDAS
*Director of the United States Patent and Trademark Office*